United States Patent
Ohishi

(10) Patent No.: US 9,345,442 B2
(45) Date of Patent: May 24, 2016

(54) SYSTEM AND DERIVATION METHOD

(71) Applicants: Kabushiki Kaisha Toshiba, Minato-ku (JP); Toshiba Medical Systems Corporation, Otawara-shi (JP)

(72) Inventor: Satoru Ohishi, Otawara (JP)

(73) Assignees: KABUSHIKI KAISHA TOSHIBA, Minato-ku (JP); Toshiba Medical Systems Corporation, Otawara-shi (JP)

( * ) Notice: Subject to any disclaimer, the term of this patent is extended or adjusted under 35 U.S.C. 154(b) by 6 days.

(21) Appl. No.: 14/337,695

(22) Filed: Jul. 22, 2014

(65) Prior Publication Data
US 2014/0334678 A1  Nov. 13, 2014

Related U.S. Application Data

(63) Continuation of application No. PCT/JP2013/080894, filed on Nov. 15, 2013.

(30) Foreign Application Priority Data

Nov. 15, 2012 (JP) .................................. 2012-251416

(51) Int. Cl.
*G06K 9/00* (2006.01)
*A61B 6/00* (2006.01)
(Continued)

(52) U.S. Cl.
CPC .............. *A61B 6/504* (2013.01); *A61B 6/5217* (2013.01); *G06T 5/002* (2013.01); *G06T 7/0014* (2013.01); *G06T 7/0016* (2013.01); *G06T 7/604* (2013.01); *A61B 6/03* (2013.01); *A61B 6/48* (2013.01); *G06T 2207/10081* (2013.01); *G06T 2207/10088* (2013.01); *G06T 2207/20036* (2013.01); *G06T 2207/20182* (2013.01);

(Continued)

(58) Field of Classification Search
None
See application file for complete search history.

(56) References Cited

U.S. PATENT DOCUMENTS

2009/0043187 A1* 2/2009 Lautenschlager ...... A61B 6/504
                                                        600/407
2009/0279752 A1* 11/2009 Sirohey .................... G06K 9/00
                                                        382/128

(Continued)

FOREIGN PATENT DOCUMENTS

JP   2005-278690 A   10/2005
JP   2008-278930 A   11/2008

(Continued)

OTHER PUBLICATIONS

Lauric et al (NPL: "Automated Detection and Classification of Intracranial Aneurysm based on 3D surface", Aug. 2010, Tufts University Publication, p. 147).*

(Continued)

*Primary Examiner* — Bhavesh Mehta
*Assistant Examiner* — Oneal R Mistry
(74) *Attorney, Agent, or Firm* — Oblon, McClelland, Maier & Neustadt, L.L.P.

(57) ABSTRACT

A system according to one embodiment includes a memory, an aneurysm identification device, a distortion-degree evaluation device, and a rupture risk derivation device. The memory stores medical image data. The aneurysm identification device identifies an aneurysm in the medical image data. The distortion-degree evaluation device quantitatively evaluates a distortion degree of the aneurysm. The rupture risk derivation device derives a rupture risk of the aneurysm from a result of the evaluation.

10 Claims, 10 Drawing Sheets

(51) Int. Cl.
*G06T 5/00* (2006.01)
*G06T 7/00* (2006.01)
*G06T 7/60* (2006.01)
*A61B 6/03* (2006.01)

(52) U.S. Cl.
CPC ........... *G06T 2207/30016* (2013.01); *G06T 2207/30101* (2013.01); *G06T 2207/30104* (2013.01)

(56) References Cited

U.S. PATENT DOCUMENTS

| | | | | |
|---|---|---|---|---|
| 2010/0284587 | A1* | 11/2010 | Malek | A61B 5/02014 382/128 |
| 2010/0309198 | A1* | 12/2010 | Kauffmann | A61B 6/504 345/419 |
| 2013/0034283 | A1* | 2/2013 | Ohishi | A61B 6/032 382/128 |
| 2014/0198131 | A1* | 7/2014 | Rudin | A61B 6/12 345/634 |

FOREIGN PATENT DOCUMENTS

| | | | | |
|---|---|---|---|---|
| JP | WO 2012023283 | A1* | 2/2012 | ............ A61B 6/032 |
| JP | 2012-110444 | A | 6/2012 | |

OTHER PUBLICATIONS

International Search Report mailed Dec. 17, 2013 for PCT/JP2013/080894 filed on Nov. 15, 2013 with English Translation.

International Written Opinion mailed Dec. 17, 2013 for PCT/JP2013/080894 filed on Nov. 15, 2013.

Yoshitaka Masutani, et al., "Fundamental Studies for Shape Irregularity Quantification of Cerebral Aneurysm: Experimental Study for Image Resolution Dependency of Shape Features", IEICE Technical Report MI2007-91, 2008, pp. 143-146.

Dhar S., et al. "Morphology parameters for intracranial aneurysm rupture assessment", Neurosurgery, 63(2), pp. 185-196, Aug. 2008.

* cited by examiner

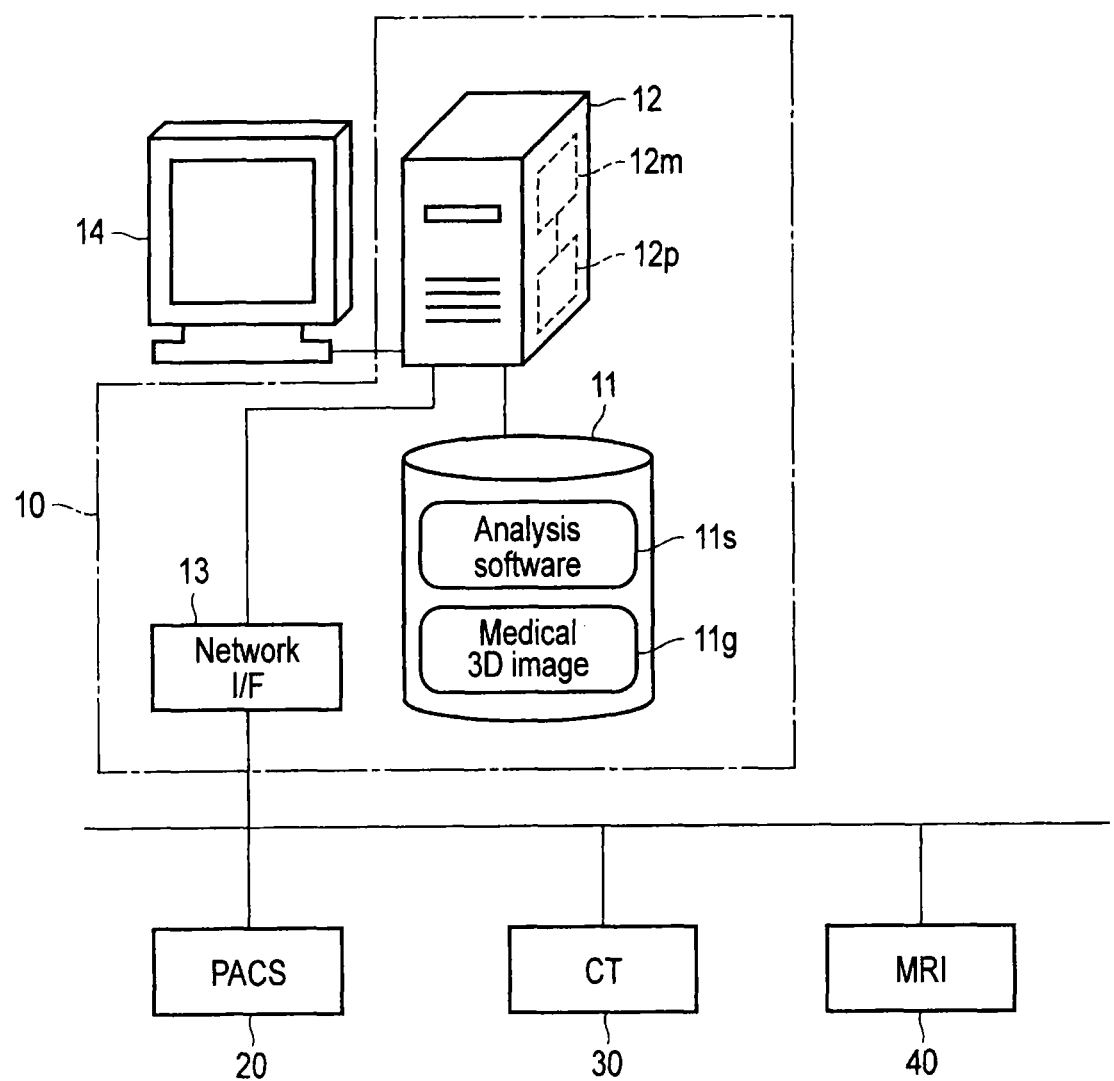
F I G. 1

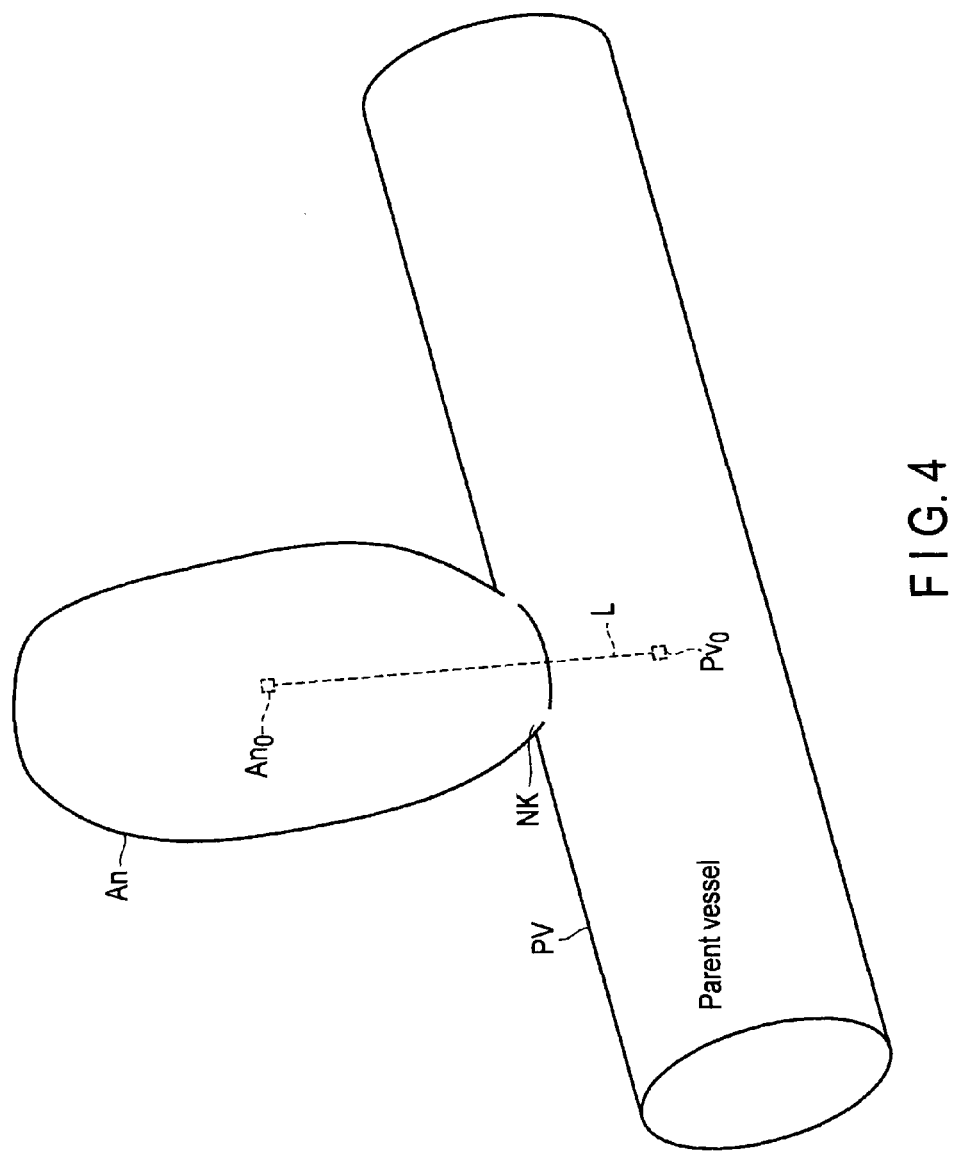
F I G. 4

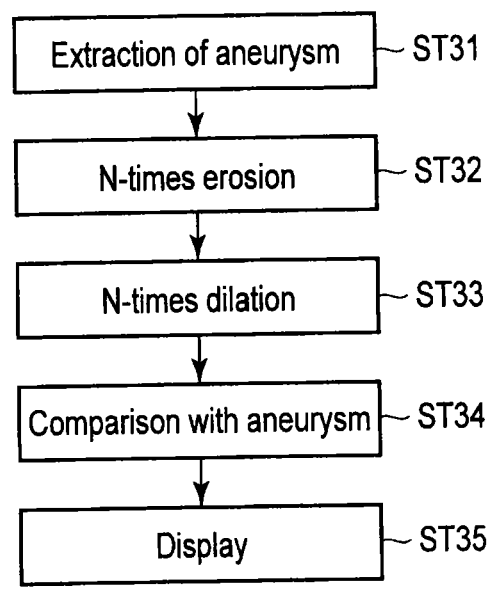
F I G. 8

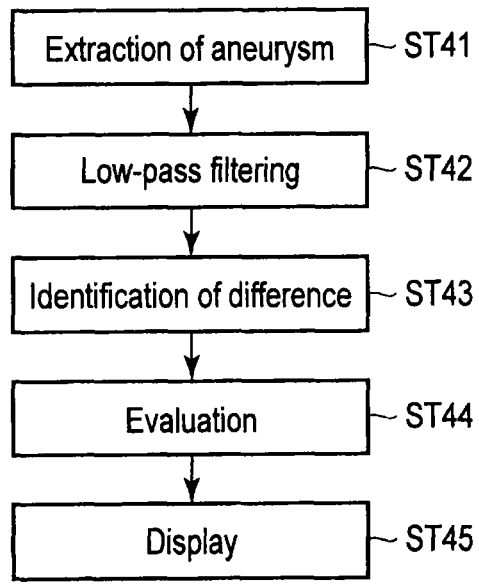
F I G. 10
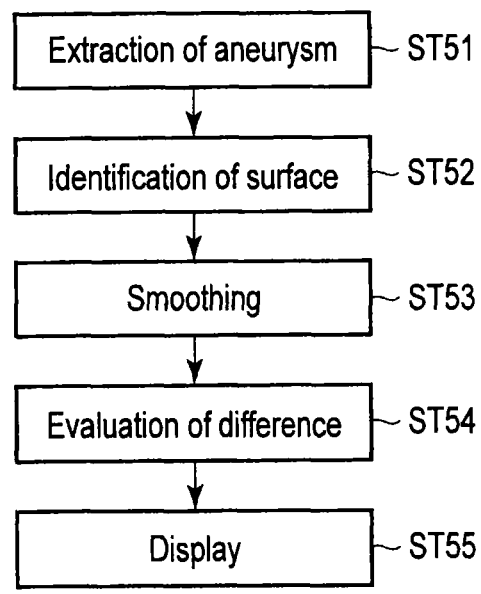
F I G. 11

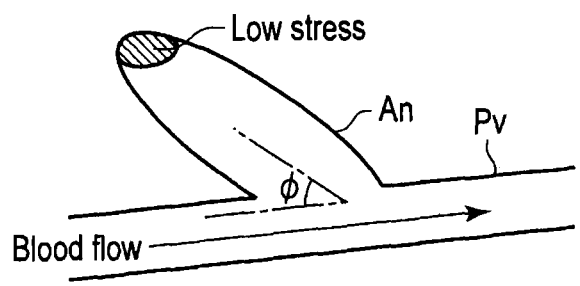
F I G. 13B
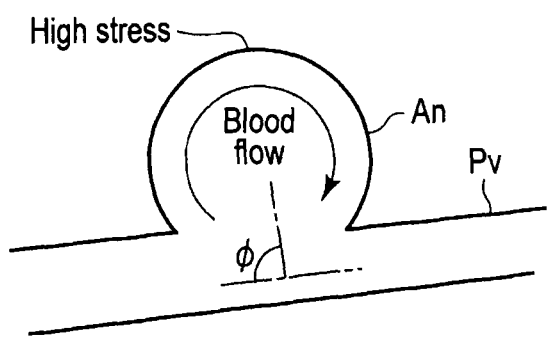
F I G. 13C

SYSTEM AND DERIVATION METHOD

CROSS-REFERENCE TO RELATED APPLICATIONS

This is a Continuation Application of PCT application No. PCT/JP2013/080894, filed on Nov. 15, 2013, which was published under PCT Article 21(2) in Japanese.

This application is based upon and claims the benefit of priority from Japanese Patent Application No. 2012-251416, filed on Nov. 15, 2012; the entire contents of which are incorporated herein by reference.

FIELD

Embodiments described herein relate generally to a system and a derivation method.

BACKGROUND

Regarding an intracranial aneurysm, in general, a surgical operation is performed when there is a high risk of a rupture (hereinafter referred to as a "rupture risk"), and follow-up treatment (observation of progress) with medication is performed when the rupture risk is low. At a time of follow-up treatment of an intracranial aneurysm, various methods are used for evaluating the morphology of the aneurysm.

A first method is a method in which an image of the aneurysm is acquired by CTA (computed tomography angiography) or MRI (magnetic resonance imaging), and the shape of the aneurysm is visually evaluated based on this image.

A second method is a method in which, based on the above-described image, the blood flow to the aneurysm is analyzed by a computer, and a shear stress of the inner wall (WSS: wall shear stress) is evaluated.

It has begun to be understood by studies in recent years that an intracranial aneurysm occurs due to an excessive pressure (stress) on the inner wall by the blood flow, and the inner wall becomes fragile due to a decrease in stress, resulting in a rupture.

Thus, according to the inventor's study, when the rupture risk of the aneurysm is to be analyzed (derived), it is useful to analyze such shape, size and distortion of an aneurysm as to decrease the stress on the inner wall.

However, a method of analyzing such shape, size and distortion of an aneurysm has not yet been proposed.

The purpose is to provide a system and a derivation method, which can analyze such shape, size and distortion of an aneurysm as to decrease the stress on the inner wall.

BRIEF DESCRIPTION OF THE DRAWINGS

FIG. 1 is a schematic view illustrating a system according to a first embodiment and a peripheral configuration thereof.

FIG. 4 is a schematic view for explaining an example of an extraction operation of an aneurysm in the embodiment.

FIG. 8 is a flowchart for explaining an operation in a third embodiment.

FIG. 10 is a flowchart for explaining an operation in a fourth embodiment.

FIG. 11 is a flowchart for explaining an operation in a fifth embodiment.

FIG. 13B is a schematic view for explaining the advantageous effect in the embodiment.

FIG. 13C is a schematic view for explaining the advantageous effect in the embodiment.

DETAILED DESCRIPTION

Figure 2:
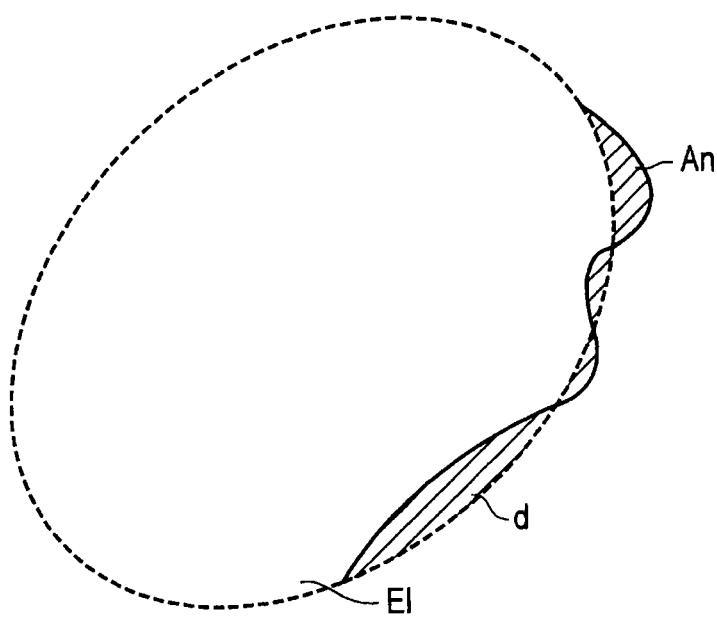
FIG. 2 is a schematic view illustrating an aneurysm, an ellipsoid and a difference between both in the embodiment.

In general, according to one embodiment, a system includes a memory, an aneurysm identification device, a distortion-degree evaluation device, and a rupture risk derivation device.

The memory stores medical image data.

The aneurysm identification device identifies an aneurysm in the medical image data.

The distortion-degree evaluation device quantitatively evaluates a distortion degree of the aneurysm.

The rupture risk derivation device derives a rupture risk of the aneurysm from a result of the evaluation.

Systems and derivation methods according to various embodiments will now be described with reference to the accompanying drawings. Each of the systems to be described below can be implemented by a hardware configuration or by a combinational configuration of hardware resources and software. As software of the combinational configuration, a program is used which is pre-installed in a computer over a network or from a storage medium in order to cause the computer to realize the respective functions of the system. Incidentally, the term "system" may be replaced with "rupture risk derivation system", "derivation system", or the like. In addition, the term "derivation" may be replaced with "analysis" or the like.

First Embodiment

FIG. 1 is a schematic view illustrating a system according to a first embodiment and a peripheral configuration thereof. The system is composed of a medical imaging workstation 10 and a monitor device 14. The medical imaging workstation 10 includes a hard disk 11, a computer 12 and a network I/F (e.g. Ethernet (trademark) card) 13.

The hard disk 11 stores analysis software (program) 11$s$, and a medical three-dimensional (3D) image (medical image data) 11$g$. The computer 12 includes a main memory 12$m$ and a processor 12$p$.

The processor 12$p$ reads out the analysis software 11$s$ and medical 3D image 11$g$, which are stored in the hard disk 11, into the main memory 12$m$, and executes the process of the analysis software 11$s$.

The processor 12$p$ acquires the medical 3D image 11$g$ from a PACS (picture archiving communication system) system 20, a CT (computed tomography) apparatus 30 and an MRI apparatus 40 from the network I/F 13 via the network, and stores them in the hard disk 11.

The processor 12$p$, however, may transfer the medical 3D image 11$g$ to the main memory 12$m$, without storing it in the hard disk 11, and may analyze the medical 3D image 11g in the main memory 12m by executing the analysis software 11s which has been read out from the hard disk 11.

The analysis software 11s includes a program which is executed by the processor 12p in order to cause the computer 12 to realize an aneurysm identification function, a distortion-degree evaluation function and a rupture risk derivation function.

In this case, the aneurysm identification function is a function of identifying an aneurysm in a medical image.

The distortion-degree evaluation function is a function of quantitatively evaluating a distortion degree of the aneurysm. In the present embodiment, as illustrated in FIG. 2, the distortion-degree evaluation function includes an approximation-by-ellipsoid function of approximating the shape of an aneurysm An by an ellipsoid El, and a difference evaluation function of evaluating a difference d between the aneurysm and ellipsoid El as the distortion degree.

The rupture risk derivation function is a function of deriving a rupture risk of the aneurysm An from the result of evaluation. In addition, the evaluation result by the distortion-degree evaluation function and a derivation result by the rupture risk derivation function are displayed on the monitor device 14.

Figure 3:
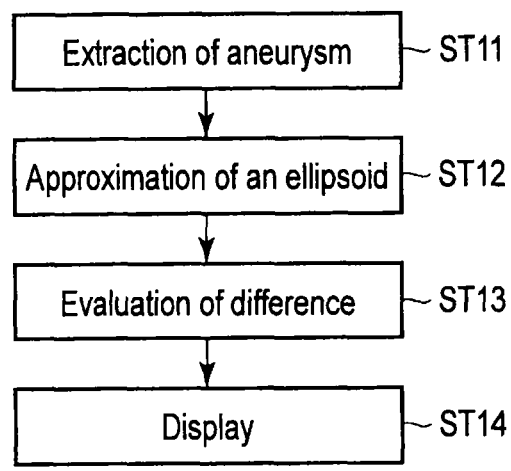
FIG. 3 is a flowchart for explaining an operation in the embodiment.
Figure 5:
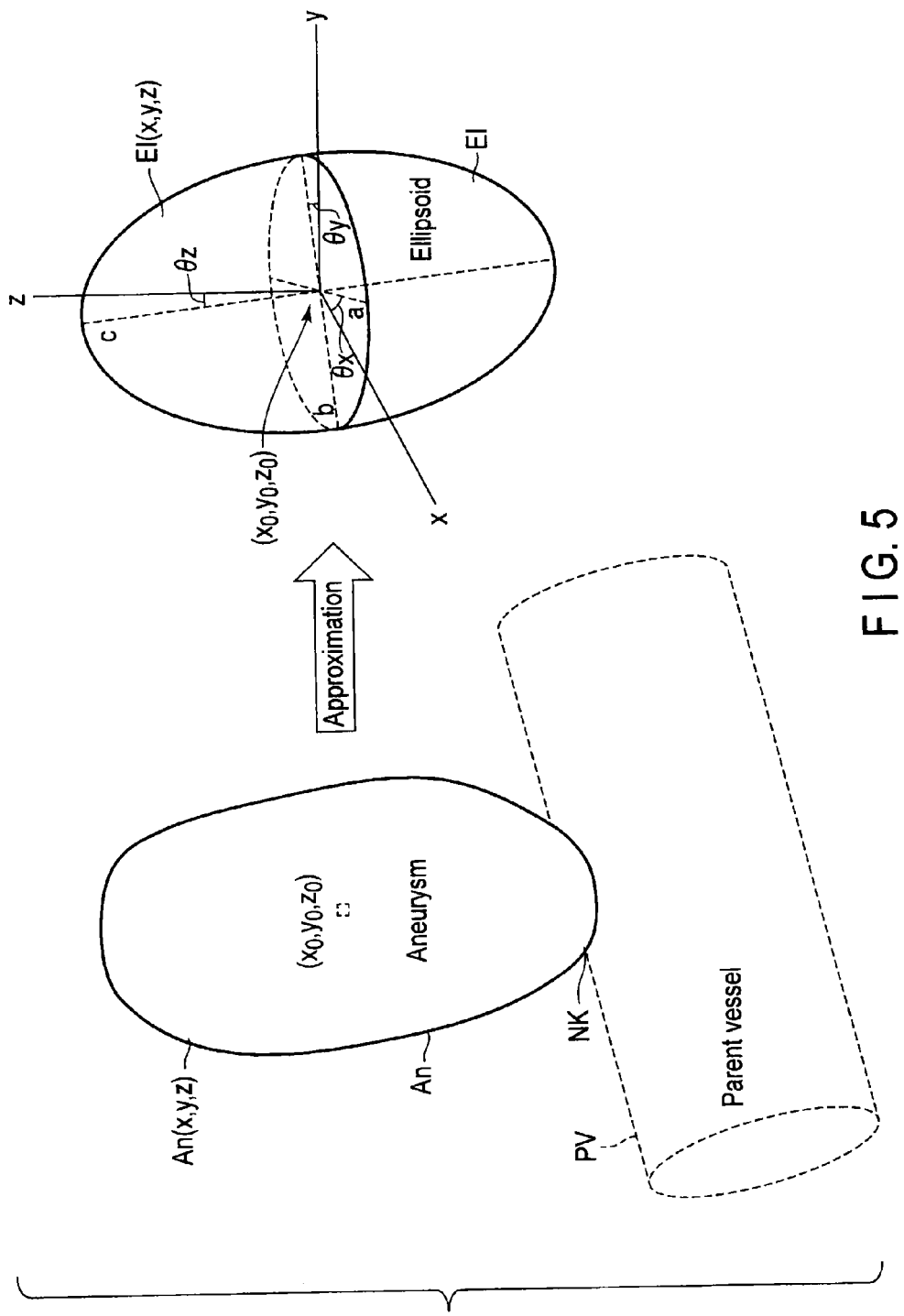
FIG. 5 is a schematic view for explaining an example of an approximation of an ellipsoid in the embodiment.

Next, the operation of the system with the above-described configuration is described with reference to a flowchart of FIG. 3 and schematic views of FIG. 4 and FIG. 5. In the medical imaging workstation 10 of the system, by the operation of an operator, the processor 12p is reading out the analysis software 11s, which is stored in the hard disk 11, into the main memory 12m, and is executing the analysis software 11s. Also, in the medical imaging workstation 10 of the system, by the operation of the operator, the processor 12p is reading out a medical 3D image 11g of an analysis target from the hard disk 11 into the main memory 12m. In addition, the processor 12p sends out this medical 3D image 11g to the monitor device 14, and the monitor device 14 is displaying this medical 3D image 11g.

le;.4qThe processor 12p extracts an aneurysm An from the medical 3D image 11g in the main memory 12m (ST11). The extraction of the aneurysm An may be executed by manual extraction by the operator with a GUI (graphical user interface) which is not shown. In addition, the extraction of the aneurysm An may be executed by a semi-automatic process in which a line segment L passing through a center An0 of the aneurysm An and a center Pv0 of a parent vessel PV is designated, as illustrated in FIG. 4, thereby automatically determining a neck NK and recognizing the center side of the aneurysm An from the neck NK as the aneurysm An. Also, the extraction of the aneurysm An may be executed by a method in which thinning of blood vessels is performed and a branch which is broken at some point along its length is found, and a variation in thickness of this branch is analyzed, thereby automatically recognizing the aneurysm An. These extraction methods of the aneurysm An are similarly applicable to the embodiments which are described below.

Next, the processor 12p approximates the aneurysm An, which has been extracted in step ST11, by an ellipsoid El (ST12). As illustrated in FIG. 5 and indicated by formulae below, the approximation is executed by identifying $(x_0, y_0, z_0)$, $(a, b, c)$ and $(\theta_x, \theta_y, \theta_z)$ so as to minimize an error E in orthogonal coordinates of an x axis, a y axis and a z axis. Also, $(x_0, y_0, z_0)$ is indicative of center coordinates of the aneurysm An and ellipsoid El, $(a, b, c)$ is indicative of half the length of the diameter in the x axis, y axis and z axis, and $(\theta_x, \theta_y, \theta_z)$ is indicative of a rotational angle in the x axis, y axis and z axis.

$$E = \|An(x,y,z) - El(x,y,z)\|^2 \quad (1)$$

where $An(x, y, z)$ represents an extracted aneurysm, and is 1 in the case of an aneurysm and is 0 in other cases. $El(x, y, z)$ is a formula of an ellipsoid, and is 1 when the following formula is satisfied and is 0 in other cases.

$$\frac{X^2}{a^2} + \frac{Y^2}{b^2} + \frac{Z^2}{c^2} < 1 \quad (2)$$

where X, Y and Z are as follows.

$$\begin{pmatrix} X \\ Y \\ Z \end{pmatrix} = \begin{pmatrix} \cos\theta_z & -\sin\theta_x & 0 \\ \sin\theta_z & \cos\theta_z & 0 \\ 0 & 0 & 1 \end{pmatrix} \quad (3)$$

$$\begin{pmatrix} \cos\theta_y & 0 & \sin\theta_y \\ 0 & 1 & 0 \\ -\sin\theta_y & 0 & \cos\theta_y \end{pmatrix} \begin{pmatrix} 1 & 0 & 0 \\ 0 & \cos\theta_x & -\sin\theta_x \\ 0 & \sin\theta_x & \cos\theta_x \end{pmatrix} \begin{pmatrix} x - x_0 \\ y - y_0 \\ z - z_0 \end{pmatrix}$$

Subsequently, the processor 12p compares the shape of the ellipsoid El and the shape of the aneurysm An, and evaluates a difference d between the aneurysm and the ellipsoid El as a distortion degree (ST13). In the evaluation method, for example, a subtraction is performed between the shape of the ellipsoid El and the shape of the aneurysm An, and the thickness at each surface position of the difference is calculated as the distortion degree.

Thereafter, the processor 12p generates image data in which a thickness region corresponding to the calculated thickness is superimposed on the surface of the aneurysm An as a color region or a high-luminance region, and sends out this image data to the monitor device 14. The monitor device 14 displays this image data (ST14).

In addition, the processor 12p may calculate a ratio between a minimum diameter and a maximum diameter by using a, b and c which have been calculated by the formula of the ellipsoid, and may output this ratio to the monitor device 14 as the distortion degree of the entire aneurysm An.

At last, the processor 12p derives the rupture risk of the aneurysm An from the evaluation result of the distortion degree, and sends out this derived result to the monitor device 14. For example, when the difference d between the aneurysm and the ellipsoid El is set to be the distortion degree, the rupture risk is derived as "high", "middle" or "low" in accordance with the magnitude of the difference d. The range of the difference d and the "high", "middle" and "low" of the rupture risk may be associated in advance and may be set in the analysis software 11s. The same applies to the embodiments described below, and the range of the evaluation result and the derived result of the rupture risk are associated in advance and are set in the analysis software 11s. The monitor device 14 displays the derived result of the rupture risk.

As has been described above, according to the present embodiment, the aneurysm An in the medical three-dimensional image (medical image data) 11g is identified, the distortion degree of the aneurysm An is quantitatively evaluated, and the rupture risk of the aneurysm An is derived from the evaluation result. By this configuration, such distortion of the aneurysm An as to decrease the stress on the inner wall can be analyzed.

If a supplementary description is given, it is considered that if there is a distortion in the shape of the aneurysm An, the blood flow stagnates at a location of the distortion and the stress on the inner wall lowers. In addition, according recent studies, a rupture occurs due to a decrease in stress. Specifically, since a distortion causes a decrease in stress and the decrease in stress causes a rupture, the rupture risk can be derived in accordance with the quantitative evaluation result of the distortion.

In addition, in the present embodiment, the shape of the aneurysm An is approximated by the ellipsoid El, and the difference between the aneurysm An and the ellipsoid El is evaluated as the distortion degree. By this configuration, the above-described advantageous effect can be obtained precisely and quickly. If a supplemental description is given, since the shape of the aneurysm An is approximated by the ellipsoid El, the above-described advantageous effect can be obtained more precisely than, for example, in the case of approximation by a sphere. In addition, since the shape of the aneurysm An is approximated by the ellipsoid El, the above-described advantageous effect can be obtained more quickly than, for example, in the case of approximation by multiple spheres in which spheres with different sizes are combined.

Second Embodiment

Next, a system according to a second embodiment is described with reference to FIG. 1. A detailed description of the same parts as in the above-described parts is omitted, and different parts will mainly be described. Similarly, a description of overlapping parts will be omitted in connection with the respective embodiments to be described below.

The second embodiment is a modification of the "distortion-degree evaluation function" in the first embodiment. In the second embodiment, the "distortion-degree evaluation function" includes, in place of the above-described "approximation-by-ellipsoid function" and "difference evaluation function", a first identification function of identifying a surface area of the aneurysm An, a tangent calculation function of calculating a tangent of the surface, and a tangent variation-degree evaluation function of evaluating a variation degree of the tangent as a distortion degree.

In this case, the tangent calculation function may include a function of approximating the surface area of a curved surface, a function of identifying a first tangent of the curved surface, and a function of identifying a plurality of second tangents near the first tangent.

In addition, the tangent variation-degree evaluation function may include a function of calculating an error between a plane, which is identified by averaging a plurality of second tangents, and the first tangent, as a variation degree.

The other configuration is the same as in the first embodiment.

Figure 6:
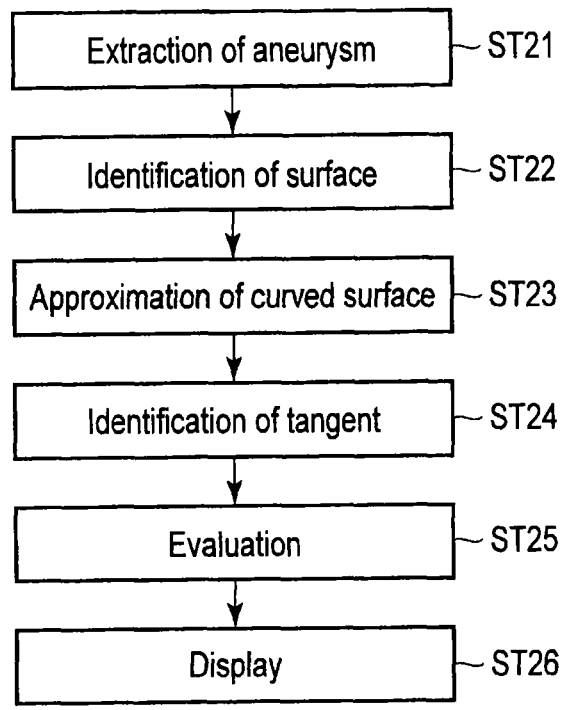
FIG. 6 is a flowchart for explaining an operation in a second embodiment.

Next, the operation of the system with the above-described configuration is described with reference to a flowchart of FIG. 6. The operations from the start to step ST21 are the same as the operations from the start to step ST11 in the first embodiment.

The processor 12p extracts an aneurysm An from the medical 3D image 11g in the main memory 12m (ST21).

Next, the processor 12p identifies a boundary of the aneurysm An as a surface (ST22).

In addition, the processor 12p calculates a tangent of the identified surface (ST23 and ST24). For example, the processor 12p approximates the identified surface by a multidimensional curved-surface formula (ST23), and identifies (calculates) a tangent from this curved-surface formula (ST24).

Further, the processor 12p compares the identified tangent with nearby tangents. In addition, the processor 12p evaluates an error between a plane, which is identified by averaging nearby tangents, and the tangent, as a variation degree (ST25).

Thereafter, the processor 12p generates image data in which a tangent with the evaluated distortion degree is superimposed on the surface of the aneurysm An as a color region or a high-luminance region, and sends out this image data to the monitor device 14. The monitor device 14 displays this image data (ST26).

Subsequently, in the same manner as described above, the processor 12p derives the rupture risk of the aneurysm An from the evaluation result of the distortion degree, and sends out this derived result to the monitor device 14. The monitor device 14 displays the derived result of the rupture risk.

As has been described above, according to the present embodiment, the configuration in which the distortion degree is evaluated is replaced with the configuration in which the surface of the aneurysm An is identified, the tangent of the surface is calculated and the variation degree of the tangent is evaluated as the distortion degree. Also in the case of this replacement of the configuration, like the first embodiment, such a distortion of the aneurysm An as to lower the stress on the inner wall can be analyzed.

The second embodiment may be modified such that the "tangent calculation function" includes a function of identifying the center of the aneurysm from the surface, a function of calculating a first vector which connects the center of the aneurysm and the surface, and a function of calculating a plurality of second vectors which connect the center of the aneurysm and a plurality of surfaces near this surface, and the "tangent variation-degree evaluation function" includes a function of calculating an error between a vector, which is identified by averaging the plural second vectors, and the first vector, as the variation degree.

Figure 7:
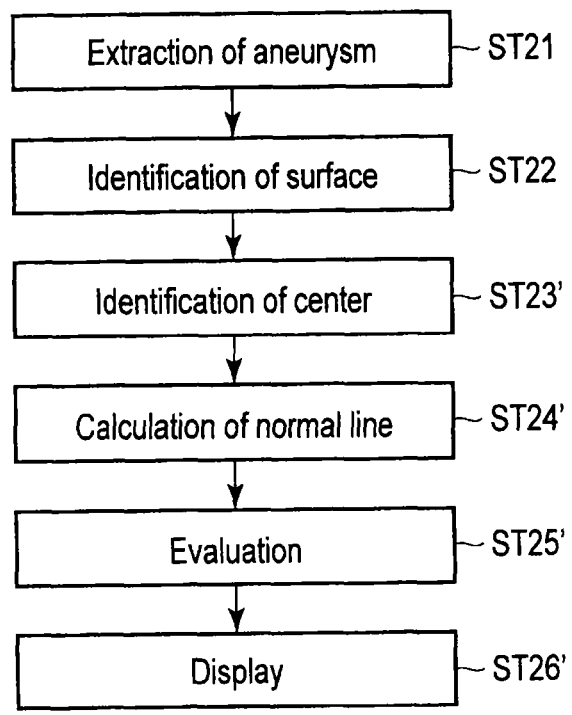
FIG. 7 is a flowchart for explaining an operation of a modification of the embodiment.

In the case of this modification, as illustrated in FIG. 7, steps ST21 and ST22 are executed as described above. Next, the processor 12p calculates the tangent of the identified surface (ST23' and ST24'). In this case, the processor 12p identifies the center of gravity of the aneurysm An from the identified surface as the center point (ST23'), and calculates a first vector, which connects this center point and the surface, as a normal line (ST24').

Further, the processor 12p evaluates an error between a vector, which is identified by averaging normal lines in nearby surfaces, and the normal line, as a distortion degree (ST25').

Thereafter, the processor 12p generates image data in which a surface with the evaluated distortion degree is superimposed on the surface of the aneurysm An as a color region or a high-luminance region, and sends out this image data to the monitor device 14. The monitor device 14 displays this image data (ST26').

The operation after the completion of step ST26' is as described above.

With this modification, the same advantageous effects as in the second embodiment can be obtained.

Third Embodiment

Next, a system according to a third embodiment is described with reference to FIG. 1.

The third embodiment is a modification of the "distortion-degree evaluation function" in the first embodiment. In the third embodiment, the "distortion-degree evaluation function" includes, in place of the above-described "approximation-by-ellipsoid function" and "difference evaluation function", a function of creating an image by executing a erosion process and an dilation process on the image of the aneurysm, and a function of comparing the created image with the image prior to the execution of the erosion process and dilation process, and evaluating a difference between both images as a distortion degree.

The other configuration is the same as in the first embodiment.

Next, the operation of the system with the above-described configuration is described with reference to a flowchart of FIG. 8. The operations from the start to step ST31 are the same as the operations from the start to step ST11 in the first embodiment.

The processor 12$p$ extracts an aneurysm An from the medical 3D image 11$g$ in the main memory 12$m$ (ST31).

Next, the processor 12$p$ executes the erosion process N times on the image of the aneurysm An (ST32). A one-time erosion process is expressed by the following formula.

$$Er\{f(i, j, k)\} = \begin{cases} 1: \text{When voxel } (i, j, k), \text{ or any one of 26} \\ \quad \text{neighbors thereof, is 0.} \\ 0: \text{At other times.} \end{cases}$$

In this case, in f(i, j, k), the aneurysm is indicative of 1, and other regions are indicative of 0.

Next, the processor 12$p$ executes the dilation process N times on the image which has been subjected to the erosion process (ST33). A one-time dilation process is expressed by the following formula.

$$D\{f(i, j, k)\} = \begin{cases} 1: \text{When voxel } (i, j, k), \text{ or any one of 26} \\ \quad \text{neighbors thereof, is 1.} \\ 0: \text{At other times.} \end{cases}$$

Further, the processor 12$p$ compares the image, which has been created by executing the erosion and dilation processes, and the original image of the aneurysm An (ST34), and evaluates a difference between both images as a distortion degree.

Thereafter, the processor 12$p$ generates image data in which a region with the evaluated distortion degree is superimposed on the surface of the aneurysm An as a color region or a high-luminance region, and sends out this image data to the monitor device 14. The monitor device 14 displays this image data (ST35).

After step ST35, the derivation operation of the rupture risk and the display operation of the derived result are executed in the same manner as described above.

Figure 9:
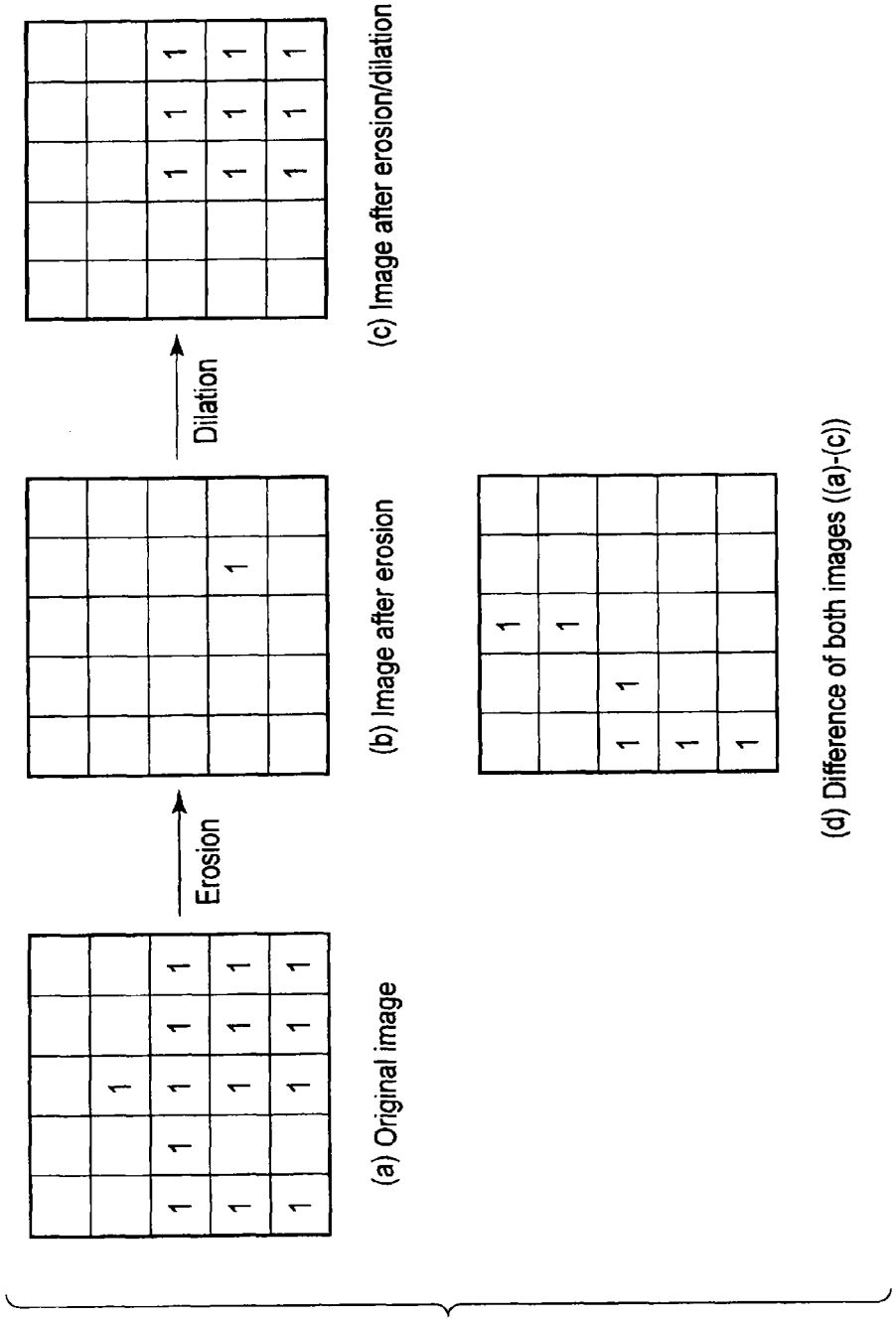
FIG. 9 is a schematic view for explaining a difference between both images in the embodiment.

In the above-described process of steps ST32 to ST34, when, for example, a one-time erosion/dilation process has been executed on an image shown in part (a) of FIG. 9, an image shown in part (c) of FIG. 9 is obtained. If a difference is obtained between the original image shown in part (a) of FIG. 9 and the image after the erosion/dilation process shown in part (c) of FIG. 9, a projecting part or a recessed part (i.e. a distorted part) in the original image is extracted, as illustrated in part (d) of FIG. 9.

Although the case in which the one-time erosion/dilation process was executed has been described, the present embodiment is not limited to this case. According to this embodiment, for example, the erosion process and dilation process may be executed N times, respectively, and the differences may be displayed in different colors. Thereby, a part extracted as a difference with a small value of N is set to be a part with a large distortion, and a part extracted as a difference with a large value of N is set to be a part with a small distortion, and thus the distortion degree can be quantified.

As has been described above, according to the present embodiment, the configuration in which the distortion degree is evaluated is replaced with the configuration in which an image is created by executing the erosion process and dilation process on the image of the aneurysm An. The created image is compared with the image prior to the execution of the erosion process and dilation process, and the distortion degree is calculated based on the difference between both images. Also in the case of this replacement of the configuration, like the first embodiment, such a distortion of the aneurysm An as to lower the stress on the inner wall can be analyzed.

Fourth Embodiment

Next, a system according to a fourth embodiment is described with reference to FIG. 1.

The fourth embodiment is a modification of the "distortion-degree evaluation function" in the first embodiment. In the fourth embodiment, the "distortion-degree evaluation function" includes, in place of the above-described "approximation-by-ellipsoid function" and "difference evaluation function", a function for creating an image by subjecting the image of the aneurysm to a low-pass filter, and a function of comparing the created image with the image before being subjected to the low-pass filter, and evaluating a difference between both images as a distortion degree.

The other configuration is the same as in the first embodiment.

Next, the operation of the system with the above-described configuration is described with reference to a flowchart of FIG. 10. The operations from the start to step ST41 are the same as the operations from the start to step ST11 in the first embodiment.

The processor 12$p$ extracts an aneurysm An from the medical 3D image 11$g$ in the main memory 12$m$ (ST41).

Next, the processor 12$p$ creates an image by subjecting the image of the aneurysm An to a low-pass filter (ST42).

In addition, the processor 12$p$ compares the created image and the image before being subjected to the low-pass filter, and identifies a difference between both images (ST43).

Subsequently, the processor 12$p$ evaluates the difference between both images as a distortion degree (ST44).

Thereafter, the processor 12$p$ generates image data in which a region with the evaluated distortion degree is superimposed on the surface of the aneurysm An as a color region or a high-luminance region, and sends out this image data to the monitor device 14. The monitor device 14 displays this image data (ST45).

After step ST45, the derivation operation of the rupture risk and the display operation of the derived result are executed in the same manner as described above.

A plurality of low-pass filters, which are used in the above-described step ST42, are prepared depending on degrees. In steps ST43 and ST44, a process result of a low-pass filter with a weak degree (i.e. less blurring) and the original aneurysm are compared, and a difference therebetween is recorded as a distorted part. Similarly, process results of low-pass filters with degrees of gradually increasing strength (i.e. more blurring) and the original aneurysm are compared, and differences therebetween are recorded as distorted parts. A part extracted as a difference at the initial stage is recorded as a part with a large distortion degree, and parts extracted as differences stepwise are recorded as parts with lower distortion degrees, and these parts are displayed in different colors. For example, a part with a large distortion degree is displayed in red, a part with a small distortion degree is displayed in blue, and an intermediate level is displayed in yellow.

As has been described above, according to the present embodiment, the configuration in which the distortion degree is evaluated is replaced with the configuration in which an image is created by subjecting the image of the aneurysm An to the low-pass filter, the created image is compared with the image before being subjected to the low-pass filter, and the difference between both images is evaluated as the distortion degree. Also in the case of this replacement of the configuration, like the first embodiment, such distortion of the aneurysm An as to lower the stress on the inner wall can be analyzed.

Fifth Embodiment

Next, a system according to a fifth embodiment is described with reference to FIG. 1.

The fifth embodiment is a modification of the "distortion-degree evaluation function" in the first embodiment. In the fifth embodiment, the "distortion-degree evaluation function" includes, in place of the above-described "approximation-by-ellipsoid function" and "difference evaluation function", a function of extracting a surface shape of the aneurysm An, a smoothing function of smoothing the surface shape, and a function of comparing the smoothed surface shape and the surface shape before the smoothing, and calculating a distortion degree, based on an error between both images.

The other configuration is the same as in the first embodiment.

Next, the operation of the system with the above-described configuration is described with reference to a flowchart of FIG. 11. The operations from the start to step ST51 are the same as the operations from the start to step ST11 in the first embodiment.

The processor 12p extracts an aneurysm An from the medical 3D image 11g in the main memory 12m (ST51).

Next, the processor 12p identifies a boundary of the aneurysm An as a surface (ST52).

In addition, the processor 12p executes smoothing on the identified surface (ST53). The smoothing may be executed by fitting a low-degree curved surface, or may be executed by using a curved surface approximation function such as B-SPLINE.

Further, based on an error between the smoothed curved surface and the surface, the processor 12p evaluates a distortion degree in accordance with the error (ST54). For example, a larger distortion degree is evaluated in proportion to a larger error.

Thereafter, the processor 12p generates image data in which a region with the evaluated distortion degree is superimposed on the surface of the aneurysm An as a color region or a high-luminance region, and sends out this image data to the monitor device 14. The monitor device 14 displays this image data (ST55).

After step ST55, the derivation operation of the rupture risk and the display operation of the derived result are executed in the same manner as described above.

As has been described above, according to the present embodiment, the configuration in which the distortion degree is evaluated is replaced with the configuration in which a surface shape of the aneurysm An is extracted, the surface shape is smoothed, the smoothed surface shape is compared with the surface shape before the smoothing, and the distortion degree is evaluated in accordance with an error between both images. Also in the case of this replacement of the configuration, like the first embodiment, such a distortion of the aneurysm An as to lower the stress on the inner wall can be analyzed.

Sixth Embodiment

Next, a system according to a sixth embodiment is described with reference to FIG. 1.

The sixth embodiment is a modification of the first embodiment. In the sixth embodiment, the above-described program is replaced with a program for causing the computer 12 to realize, in place of the above-described "distortion-degree evaluation function", a vessel identification function of identifying a parent vessel in which an aneurysm occurs, and an inclination evaluation function of quantitatively evaluating an inclination between the aneurysm and the parent vessel.

In this case, the inclination evaluation function may include a function of approximating the shape of the aneurysm by an ellipsoid, a function of identifying an inclination of the parent vessel, a function of calculating angles formed between the inclination of the parent vessel and diameters of the ellipsoid, and determining which of a formed angle among the formed angles is closest to a perpendicular, to be the inclination between the aneurysm and the parent vessel.

The other configuration is the same as in the first embodiment.

Figure 12:
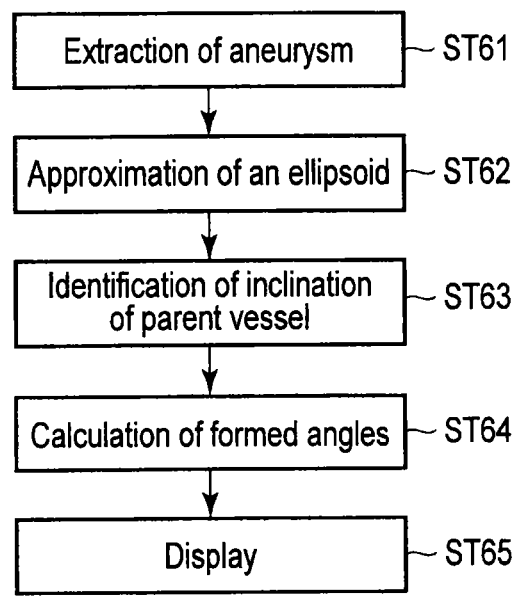
FIG. 12 is a flowchart for explaining an operation in a sixth embodiment.

Next, the operation of the system with the above-described configuration is described with reference to a flowchart of FIG. 12. The operations from the start to step ST62 are the same as the operations from the start to step ST12 in the first embodiment.

The processor 12p extracts an aneurysm An from the medical 3D image 11g in the main memory 12m (ST61), and approximates the aneurysm An by an ellipsoid El (ST62).

In addition, the processor 12p identifies the inclination of the parent vessel in which the aneurysm An occurs (ST63). The process of identifying the inclination of the parent vessel may be executed such that the inclination is identified by performing line-thinning in the vicinity of the position of the aneurysm An after the aneurysm An is deleted from the medical 3D image 11g, or the inclination is designated by the operator.

Further, the processor 12p calculates angles formed between the identified inclination and the respective axes of the ellipsoid (ST64), and determines (evaluates) an angle among the formed angles, which is closest to a perpendicular, to be the angle formed between the aneurysm and the parent vessel.

In addition, the processor 12p generates image data in which a value of the formed angle, which has been determined, is indicated in the vicinity of the neck of the aneurysm An, and sends out this image data to the monitor device 14. The monitor device 14 displays this image data (ST65).

After step ST65, the derivation operation of the rupture risk and the display operation of the derived result are executed in the same manner as described above.

As has been described above, according to the present embodiment, the aneurysm An in the medical 3D image 11g is identified, the parent vessel in which the aneurysm An occurs is identified, the inclination between the aneurysm An and the parent vessel is quantitatively evaluated, and the rupture risk of the aneurysm An is derived from the result of the evaluation. By this configuration, such a distortion of the aneurysm An as to lower the stress on the inner wall can be analyzed.

Figure 13A:
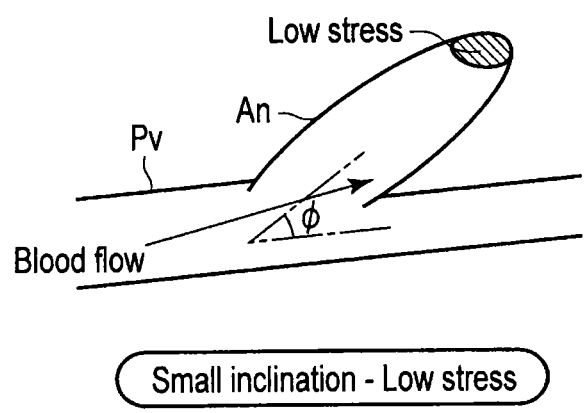
FIG. 13A is a schematic view for explaining an advantageous effect in the embodiment.

If a supplementary description is given, as illustrated in FIG. 13A or FIG. 13B, when the aneurysm An has a shape with a small inclination φ from the parent vessel Pv, it is considered that the blood flow stagnates at a location at the distal end of the aneurysm An and the stress on the inner wall decreases (conversely, as illustrated in FIG. 13C, if the inclination φ is large, it is considered that the blood flow does not stagnate and the stress on the inner wall does not decrease). In addition, according to studies in recent years, a rupture occurs due to a decrease in stress. Specifically, since a shape with a small inclination φ with respect to the parent vessel Pv causes a decrease in stress and the decrease in stress causes a rupture, the rupture risk can be derived in accordance with a quantitative evaluation result of the shape of the aneurysm An. In addition, in the case where the direction of the blood flow is also taken into account in the shape illustrated in FIG. 13A or FIG. 13B, since the blood flow tends to easily enter the aneurysm An in the shape shown in FIG. 13A than in the shape shown in FIG. 13B, it is considered that the stress decreases less easily in the shape shown in FIG. 13A. In this case, the direction of the blood flow may be determined by the processor 12p to be, for example, a direction of flow from a thick part to a thin part of the parent vessel Pv, or may be designated by the operator.

Seventh Embodiment

Next, a system according to a seventh embodiment is described with reference to FIG. 1.

The seventh embodiment is a modification of each of the first to sixth embodiments. In the seventh embodiment, the "aneurysm identification function" of the above-described program includes a function of identifying an aneurysm An at an identical position in two or more medical 3D images 11g in an identical subject.

In the case where the seventh embodiment is a modification of each of the first to fifth embodiments, the above-described "distortion-degree evaluation function" includes a function of evaluating a variation of the distortion degree of the identified aneurysm An.

In addition, the above-described program is replaced with a program which causes the computer 12 to further function as a size evaluation function and an output function. The size evaluation function is a function of evaluating a variation of the size (e.g. volume, surface area) of the identified aneurysm An. The output function is a function of outputting an evaluation result of either the size evaluation function or the distortion-degree evaluation function, or evaluation results of both the functions.

On the other hand, in the case where the seventh embodiment is a modification of the sixth embodiment, the above-described "inclination evaluation function" includes a function of evaluating a variation of the inclination φ between the identified aneurysm An and parent vessel Pv.

Also, the above-described program is replaced with a program which causes the computer 12 to further function as a size evaluation function and an output function. The size evaluation function is a function of evaluating a variation of a size of the identified aneurysm An. The output function is a function of outputting an evaluation result of either the size evaluation function or the inclination evaluation function, or evaluation results of both the functions.

The other configuration is the same as in the first embodiment.

Next, the operation of the system with the above-described configuration is described.

The processor 12p extracts an aneurysm An from a plurality of medical 3D images 11g, and displays an evaluation result on the monitor device 14 so as to be able to compare a volume of this aneurysm An and a distortion degree calculated by using any one of the above-described first to fifth embodiments (or an inclination calculated by using the sixth embodiment).

For example, time may be displayed on the abscissa of a graph, and the volume, the distortion degree (or inclination) of the entire aneurysm An or a maximum value of a local distortion degree may be displayed on the ordinate of the graph. Either the volume or the distortion degree, or both of them may be displayed as needed. Similarly, either the volume or the inclination, or both of them may be displayed as needed.

In addition, the processor 12p may identify, for example, the center of the aneurysm An, map a local distortion degree at polar coordinates from the center, calculate a ratio or a variation ratio of distortion degrees at different times, and display the calculation result on the monitor device 14. In this case, the ratio r or variation ratio $r_c$ of distortion degrees $d_1$, $d_2$ at different times $t_1$, $t_2$ may be calculated, for example, as follows (where $t_1 < t_2$).

$$r = d_2/d_1$$

$$r_c = (d_2 - d_1)/(t_2 - t_1).$$

In the case of comparing two medical 3D images 11g, if a color region corresponding to the ratio or the variation ratio is superimposed on the image surface of the latest aneurysm An and is displayed, the variation of the distortion degree can be well understood.

Alternatively, the processor 12p may identify the center of the aneurysm An, identify distances from the center in a polar coordinate system from the center, calculate the ratio or the variation ratio between the distances at different times in the same manner as described above, and display the calculation result on the monitor device 14.

As has been described above, according to the present embodiment, the variation over time of the evaluation result can be displayed, in addition to the advantageous effects of each of the first to sixth embodiments.

According to at least one of the above-described embodiments, the aneurysm An in the medical 3D image 19g is identified, the distortion degree (or inclination) of the aneurysm An is quantitatively evaluated, and the rupture risk of the aneurysm An is derived from the evaluation result. By this configuration, such a distortion of the aneurysm An as to decrease the stress on the inner wall can be analyzed.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A system comprising:
   a memory configured to store medical image data;
   an aneurysm identification device which identifies an aneurysm in the medical image data;
   a distortion-degree evaluation device which quantitatively evaluates a distortion degree of the aneurysm; and
   a rupture risk derivation device which derives a rupture risk of the aneurysm from a result of the evaluation;
   wherein the distortion-degree evaluation device includes:
      an approximation-by-ellipsoid device which approximates a shape of the aneurysm by a shape of an ellipsoid; and a difference evaluation device which performs a subtraction between the shape of aneurysm and the shape of the ellipsoid and evaluates a thickness at each surface position of a difference between the aneurysm and the ellipsoid as the distortion degree.

2. A system comprising:
a memory configured to store medical image data;
an aneurysm identification device which identifies an aneurysm in the medical image data;
a distortion-degree evaluation device which quantitatively evaluates a distortion degree of the aneurysm; and
a rupture risk derivation device which derives a rupture risk of the aneurysm from a result of the evaluation;
wherein the distortion-degree evaluation device includes:
a surface identification device which identifies a surface of the aneurysm;
a tangent calculation device which calculates a tangent of the surface; and
a tangent variation-degree evaluation device which evaluates a variation degree of the tangent as the distortion degree.

3. The system according to claim 2, wherein the tangent calculation device includes a processor configured to:
approximate the surface area of a curved surface;
identify a first tangent of the curved surface; and
identify a plurality of second tangents near the first tangent, and
the tangent variation-degree evaluation device includes:
a processor configured to calculate an error between a plane, which is identified by averaging the plurality of second tangents, and the first tangent, as the variation degree.

4. The system according to claim 2, wherein the tangent calculation device includes a processor configured to:
identify a center of the aneurysm from the surface;
calculate a first vector which connects the center of the aneurysm and the surface; and
calculate a plurality of second vectors which connect the center of the aneurysm and a plurality of surfaces near the surface, and
the tangent variation-degree evaluation device includes:
a processor configured to calculate an error between a vector, which is identified by averaging the plurality of second vectors, and the first vector, as the variation degree.

5. A system comprising:
a memory configured to store medical image data;
an aneurysm identification device which identifies an aneurysm in the medical image data;
a distortion-degree evaluation device which quantitatively evaluates a distortion degree of the aneurysm; and
a rupture risk derivation device which derives a rupture risk of the aneurysm from a result of the evaluation;
wherein the distortion-degree evaluation device includes a processor configured to:
create an image by executing a erosion process and an dilation process on the image of the aneurysm; and
compare the created image with the image prior to the execution of the erosion process and dilation process, and evaluates a difference between both images as the distortion degree.

6. A system comprising:
a memory configured to store medical image data;
an aneurysm identification device which identifies an aneurysm in the medical image data;
a distortion-degree evaluation device which quantitatively evaluates a distortion degree of the aneurysm; and
a rupture risk derivation device which derives a rupture risk of the aneurysm from a result of the evaluation;
wherein the distortion-degree evaluation device includes a processor configured to:
extract a surface shape of the aneurysm;
execute smoothing on the surface shape; and
compare the smoothed surface shape and the surface shape before the smoothing, and evaluates the distortion degree, based on an error between both surface shapes.

7. A system comprising:
a memory configured to store medical image data;
an aneurysm identification device which identifies an aneurysm in the medical image data;
a vessel identification device which identifies a parent vessel in which the aneurysm occurs; and
an inclination evaluation device which quantitatively evaluates an inclination between the aneurysm and the parent vessel;
wherein the inclination evaluation device includes a processor configured to:
approximate a shape of the aneurysm by a shape of an ellipsoid;
identify an inclination of the parent vessel;
calculate angles formed between the inclination of the parent vessel and diameters of the ellipsoid; and
determine a formed angle among the formed angles, which is closest to a perpendicular, to be an inclination between the aneurysm and the parent vessel.

8. The system according to claim 7, wherein the aneurysm identification device includes a device which identifies an aneurysm at an identical position in two or more medical image data in an identical subject,
the inclination evaluation device includes a device which evaluates a variation of an inclination between the identified aneurysm and the parent vessel, and
the system includes:
a size evaluation device which evaluates a variation of a size of the identified aneurysm; and
an output device which outputs an evaluation result of either the size evaluation device or the inclination evaluation device, or evaluation results of both the size evaluation device and the inclination evaluation device.

9. The system according to claim 8, wherein the evaluation result includes a graph indicative of the variation, or either a variation ratio or a ratio indicative of the variation or both of the variation ratio and the ratio.

10. A derivation method which is executed by a system including a memory configured to store medical image data, comprising:
identifying an aneurysm in the medical image data;
quantitatively evaluating a distortion degree of the aneurysm; and
deriving a rupture risk of the aneurysm from a result of the evaluating;
wherein the evaluating the distortion degree includes:
approximating a shape of the aneurysm by a shape of an ellipsoid; and
performing a subtraction between the shape of aneurysm and the shape of the ellipsoid and evaluating a thickness at each surface position of a difference between the aneurysm and the ellipsoid as the distortion degree.

* * * * *